United States Patent
Lands et al.

(10) Patent No.: US 6,960,210 B2
(45) Date of Patent: *Nov. 1, 2005

(54) LAPAROSCOPIC BIPOLAR ELECTROSURGICAL INSTRUMENT

(75) Inventors: Michael John Lands, Clearwater, FL (US); Stephen Wade Lukianow, Boulder, CO (US); Donald Robert Loeffler, Louisville, CO (US); James Steven Cunnigham, Boulder, CO (US); Kate Ryland Lawes, Superior, CO (US); Daniel Lee Trimberger, II, Greeley, CO (US); Mathew Erle Mitchell, Boulder, CO (US); Jenifer Serafin Kennedy, Boulder, CO (US)

(73) Assignee: Sherwood Services AG, Schaffhausen (CH)

( * ) Notice: Subject to any disclaimer, the term of this patent is extended or adjusted under 35 U.S.C. 154(b) by 0 days.

This patent is subject to a terminal disclaimer.

(21) Appl. No.: 10/243,274

(22) Filed: Sep. 13, 2002

(65) Prior Publication Data

US 2003/0032956 A1 Feb. 13, 2003

Related U.S. Application Data

(63) Continuation of application No. 09/591,330, filed on Jun. 9, 2000, now Pat. No. 6,451,018, which is a continuation of application No. 08/970,472, filed on Nov. 14, 1997, now Pat. No. 6,228,083.

(51) Int. Cl.[7] .............................................. A61B 18/14
(52) U.S. Cl. ............................ 606/50; 606/46; 606/48; 606/51; 606/207; 606/208
(58) Field of Search .............................. 606/46, 48–52, 606/170, 207, 208

(56) References Cited

U.S. PATENT DOCUMENTS

| 371,664 A | 10/1887 | Brannan et al. |
|---|---|---|
| 702,472 A | 6/1902 | Pignolet |
| 728,883 A | 5/1903 | Downes |

(Continued)

FOREIGN PATENT DOCUMENTS

| CA | 2104423 | 2/1994 |
|---|---|---|
| DE | 19608716 | 4/1997 |
| EP | 0364216 A1 | 4/1990 |

(Continued)

OTHER PUBLICATIONS

US 6,090,109, 7/2000, Lands et al. (withdrawn)

(Continued)

*Primary Examiner*—Lee S. Cohen

(57) ABSTRACT

A laparoscopic bipolar electrosurgical instrument can apply a large closure force between its jaw without damaging the small yoke assembly. The instrument comprises: a first jaw having a first flange with a first slot, and a second jaw having a second flange with a second slot, wherein the first and second jaws are located at a distal end of the instrument and comprise an electrically conductive material for conducting bipolar electrosurgical current therebetween; a yoke attached to a pushrod and positioned to electrically insulate the first flange from the second flange, the yoke having a first side facing the first flange and a second side facing the second flange, the yoke further comprising a first shoulder and a second shoulder; a first pin located on the first side and movably engaged with the first slot; a second pin located on the second side and movably engaged with the second slot; the first slot and the second slot shaped such that an angle, subtended by the first and second jaws, decreases with distal motion of the pushrod, and first and second cul-de-sacs positioned respectively in the first and second slots to relive shear stresses on the first and second pins approximately when the first and second shoulders respectively engage the first and second flanges to provide a closure force between the first and second jaws.

5 Claims, 5 Drawing Sheets

U.S. PATENT DOCUMENTS

| | | |
|---|---|---|
| 1,586,645 A | 6/1926 | Bierman |
| 2,002,594 A | 5/1935 | Wappler et al. |
| 2,011,169 A | 5/1935 | Wappler |
| 2,176,479 A | 10/1939 | Willis |
| 2,305,156 A | 12/1942 | Grubel |
| 2,632,661 A | 12/1953 | Cristofv |
| 2,668,538 A | 2/1954 | Baker |
| 2,796,065 A | 6/1957 | Kapp |
| 3,459,187 A | 8/1969 | Pallotta |
| 3,643,663 A | 2/1972 | Sutter |
| 3,651,811 A | 3/1972 | Hildebrandt et al. |
| 3,862,630 A | 1/1975 | Balamuth |
| 3,866,610 A | 2/1975 | Kletschka |
| 3,911,766 A | 10/1975 | Fridolph et al. |
| 3,920,021 A | 11/1975 | Hitebrandt |
| 3,921,641 A | 11/1975 | Hulka |
| 3,938,527 A | 2/1976 | Rioux et al. |
| 3,952,749 A | 4/1976 | Fridolph et al. |
| 4,005,714 A | 2/1977 | Hiltebrandt |
| 4,074,718 A | 2/1978 | Morrison, Jr. |
| 4,088,134 A | 5/1978 | Mazzariello |
| 4,165,746 A | 8/1979 | Burgin |
| 4,300,564 A | 11/1981 | Furihata |
| 4,370,980 A | 2/1983 | Lottick |
| D276,790 S | 12/1984 | Laske |
| 4,492,231 A | 1/1985 | Auth |
| 4,552,143 A | 11/1985 | Lottick |
| 4,574,804 A | 3/1986 | Kurwa |
| 4,597,379 A | 7/1986 | Kihn et al. |
| 4,657,016 A | 4/1987 | Garito et al. |
| 4,671,274 A | 6/1987 | Sorochenko |
| 4,685,459 A | 8/1987 | Koch et al. |
| 4,763,669 A | 8/1988 | Jaeger |
| 4,827,929 A | 5/1989 | Hodge |
| 4,887,612 A | 12/1989 | Esser et al. |
| 4,938,761 A | 7/1990 | Ensslin |
| 5,007,908 A | 4/1991 | Rydell |
| 5,026,370 A | 6/1991 | Lottick |
| 5,099,840 A | 3/1992 | Goble et al. |
| 5,116,332 A | 5/1992 | Lottick |
| 5,151,102 A | 9/1992 | Kamiyama et al. |
| 5,176,695 A | 1/1993 | Dulebohn |
| 5,197,964 A | 3/1993 | Parins |
| 5,215,101 A | 6/1993 | Jacobs et al. |
| 5,217,457 A | 6/1993 | Delahuerga et al. |
| 5,217,458 A | 6/1993 | Parins |
| 5,244,462 A | 9/1993 | Delahuerga et al. |
| 5,250,047 A | 10/1993 | Rydell |
| 5,258,006 A | 11/1993 | Rydell et al. |
| 5,261,918 A | 11/1993 | Phillips et al. |
| 5,275,615 A | 1/1994 | Rose |
| 5,277,201 A | 1/1994 | Stern |
| 5,282,799 A | 2/1994 | Rydell |
| 5,290,286 A | 3/1994 | Parins |
| 5,304,203 A | 4/1994 | El-Mallawany et al. |
| 5,308,357 A | 5/1994 | Lichtman |
| 5,318,589 A | 6/1994 | Lichtman |
| 5,324,289 A | 6/1994 | Eggers |
| 5,330,471 A | 7/1994 | Eggers |
| 5,334,183 A | 8/1994 | Wuchinich |
| 5,334,215 A | 8/1994 | Chen |
| 5,336,221 A | 8/1994 | Anderson |
| 5,342,359 A | 8/1994 | Rydell |
| 5,342,381 A | 8/1994 | Tidemand |
| 5,342,393 A | 8/1994 | Stack |
| 5,352,222 A | 10/1994 | Rydell |
| 5,354,271 A | 10/1994 | Voda |
| 5,356,408 A | 10/1994 | Rydell |
| 5,366,477 A | 11/1994 | LeMarie, III et al. |
| 5,383,897 A | 1/1995 | Wholey |
| 5,389,098 A | 2/1995 | Tsuruta et al. |
| 5,389,104 A | 2/1995 | Hahnen et al. |
| 5,391,166 A | 2/1995 | Eggers |
| 5,391,183 A | 2/1995 | Janzen et al. |
| 5,403,312 A | 4/1995 | Yates et al. |
| 5,411,519 A | 5/1995 | Tovey et al. |
| 5,411,520 A | 5/1995 | Nash et al. |
| 5,413,571 A | 5/1995 | Katsaros et al. |
| 5,415,657 A | 5/1995 | Taymor-Luria |
| 5,423,810 A | 6/1995 | Goble et al. |
| 5,425,739 A | 6/1995 | Jessen |
| 5,429,616 A | 7/1995 | Schaffer |
| 5,431,674 A | 7/1995 | Basile et al. |
| 5,437,292 A | 8/1995 | Kipshidze et al. |
| 5,438,302 A | 8/1995 | Goble |
| 5,441,517 A | 8/1995 | Kensey et al. |
| 5,443,463 A | 8/1995 | Stern et al. |
| 5,443,464 A | 8/1995 | Russell et al. |
| 5,443,480 A | 8/1995 | Jacobs et al. |
| 5,445,638 A | 8/1995 | Rydell |
| 5,445,658 A | 8/1995 | Durrfeld et al. |
| 5,451,224 A | 9/1995 | Goble et al. |
| 5,456,684 A | 10/1995 | Schmidt et al. |
| 5,458,598 A | 10/1995 | Feinberg et al. |
| 5,460,629 A | 10/1995 | Shlain et al. |
| 5,462,546 A | 10/1995 | Rydell |
| 5,472,443 A | 12/1995 | Cordis et al. |
| 5,478,351 A | 12/1995 | Meade et al. |
| 5,484,436 A | 1/1996 | Eggers et al. |
| 5,496,317 A | 3/1996 | Goble et al. |
| 5,499,997 A | 3/1996 | Sharpe et al. |
| 5,509,922 A | 4/1996 | Aranyi et al. |
| 5,514,134 A | 5/1996 | Rydell et al. |
| 5,527,313 A | 6/1996 | Scott et al. |
| 5,531,744 A | 7/1996 | Nardella et al. |
| 5,540,684 A | 7/1996 | Hassler, Jr. |
| 5,540,685 A | 7/1996 | Parins et al. |
| 5,540,715 A | 7/1996 | Katsaros et al. |
| 5,558,672 A | 9/1996 | Edwards et al. |
| 5,569,241 A | 10/1996 | Edwards |
| 5,569,243 A | 10/1996 | Kortenbach et al. |
| 5,571,100 A | 11/1996 | Goble et al. |
| 5,573,535 A | 11/1996 | Viklund |
| 5,585,896 A | 12/1996 | Yamazaki et al. |
| 5,590,570 A | 1/1997 | LeMaire, III et al. |
| 5,603,711 A | 2/1997 | Parins et al. |
| 5,603,723 A | 2/1997 | Aranyi et al. |
| 5,626,578 A | 5/1997 | Tihon |
| 5,630,833 A | 5/1997 | Katsaros et al. |
| 5,637,110 A | 6/1997 | Pennybacker et al. |
| 5,643,294 A | 7/1997 | Tovey et al. |
| 5,647,869 A | 7/1997 | Goble et al. |
| 5,649,959 A | 7/1997 | Hannam et al. |
| 5,658,281 A | 8/1997 | Heard |
| 5,667,526 A | 9/1997 | Levin |
| 5,674,220 A | 10/1997 | Fox et al. |
| 5,693,051 A | 12/1997 | Schulze et al. |
| 5,695,522 A | 12/1997 | LeMaire, III et al. |
| 5,700,261 A | 12/1997 | Brinkerhoff |
| 5,702,390 A | 12/1997 | Austin et al. |
| 5,707,369 A | 1/1998 | Vaitekunas et al. |
| 5,709,680 A | 1/1998 | Yates et al. |
| 5,727,428 A | 3/1998 | LeMaire, III et al. |
| 5,743,906 A | 4/1998 | Parins et al. |
| 5,755,717 A | 5/1998 | Yates et al. |
| 5,766,166 A | 6/1998 | Hooven |
| 5,766,170 A | 6/1998 | Eggers |
| 5,769,849 A | 6/1998 | Eggers |
| 5,776,128 A | 7/1998 | Eggers |
| 5,776,130 A | 7/1998 | Buysse et al. |
| 5,779,701 A | 7/1998 | McBrayer et al. |

| | | |
|---|---|---|
| 5,792,137 A | 8/1998 | Carr et al. |
| 5,792,177 A | 8/1998 | Kaseda |
| 5,797,958 A | 8/1998 | Yoon |
| 5,800,449 A | 9/1998 | Wales |
| 5,810,808 A | 9/1998 | Eggers |
| 5,810,811 A | 9/1998 | Yates et al. |
| 5,814,043 A | 9/1998 | Shapeton |
| 5,827,271 A | 10/1998 | Buysse et al. |
| 5,827,279 A | 10/1998 | Hughett et al. |
| 5,827,281 A | 10/1998 | Levin |
| 5,833,690 A | 11/1998 | Yates et al. |
| 5,843,080 A | 12/1998 | Fleenor et al. |
| 5,849,022 A | 12/1998 | Sakashita et al. |
| 5,853,412 A | 12/1998 | Mayenberger |
| 5,876,401 A | 3/1999 | Schulze et al. |
| 5,891,141 A | 4/1999 | Rydell |
| 5,891,142 A | 4/1999 | Eggers et al. |
| 5,893,863 A | 4/1999 | Yoon |
| 5,893,875 A | 4/1999 | Oconnor et al. |
| 5,902,301 A | 5/1999 | Olig |
| 5,908,420 A | 6/1999 | Parins et al. |
| 5,913,874 A | 6/1999 | Berns et al. |
| 5,921,984 A | 7/1999 | Sutcu et al. |
| 5,935,126 A | 8/1999 | Riza |
| 5,951,549 A | 9/1999 | Richardson et al. |
| 5,954,720 A | 9/1999 | Wilson et al. |
| 5,976,132 A | 11/1999 | Morris |
| 5,989,277 A | 11/1999 | LeMaire, III et al. |
| 6,004,335 A | 12/1999 | Vaitekunas et al. |
| 6,024,744 A | 2/2000 | Kese et al. |
| 6,033,399 A | 3/2000 | Gines |
| 6,039,733 A | 3/2000 | Buysse et al. |
| 6,050,996 A | 4/2000 | Schmaltz et al. |
| 6,053,914 A | 4/2000 | Eggers et al. |
| 6,053,933 A | 4/2000 | Balazs et al. |
| D424,694 S | 5/2000 | Tetzlaff et al. |
| D425,201 S | 5/2000 | Tetzlaff et al. |
| RE36,795 E | 7/2000 | Rydell |
| 6,083,223 A | 7/2000 | Baker |
| 6,086,586 A | 7/2000 | Hooven |
| 6,090,107 A | 7/2000 | Borgmeier et al. |
| 6,099,550 A | 8/2000 | Yoon |
| 6,102,909 A | 8/2000 | Chen et al. |
| 6,110,171 A | 8/2000 | Rydell |
| 6,113,596 A | 9/2000 | Hooven et al. |
| 6,113,598 A | 9/2000 | Baker |
| H1904 H | 10/2000 | Yates et al. |
| 6,126,658 A | 10/2000 | Baker |
| 6,152,923 A | 11/2000 | Ryan |
| 6,174,309 B1 | 1/2001 | Wrublewski et al. |
| 6,179,834 B1 | 1/2001 | Buysse et al. |
| 6,179,837 B1 | 1/2001 | Hooven |
| 6,183,467 B1 | 2/2001 | Shapeton et al. |
| 6,187,003 B1 | 2/2001 | Buysse et al. |
| 6,190,386 B1 | 2/2001 | Rydell |
| 6,193,718 B1 | 2/2001 | Kortenbach et al. |
| 6,206,877 B1 | 3/2001 | Kese et al. |
| 6,224,593 B1 | 5/2001 | Ryan et al. |
| 6,228,080 B1 | 5/2001 | Gines |
| 6,228,083 B1 | 5/2001 | Lands et al. |
| 6,267,761 B1 | 7/2001 | Ryan |
| 6,273,887 B1 | 8/2001 | Yamauchi et al. |
| 6,277,117 B1 | 8/2001 | Tetzlaff et al. |
| D449,886 S | 10/2001 | Tetzlaff et al. |
| 6,334,861 B1 | 1/2002 | Chandler et al. |
| 6,350,264 B1 | 2/2002 | Hooven |
| 6,352,536 B1 | 3/2002 | Buysse et al. |
| 6,409,728 B1 | 6/2002 | Ehr et al. |
| H2037 H | 7/2002 | Yates et al. |
| 6,443,970 B1 | 9/2002 | Schulze et al. |
| 6,451,018 B1 * | 9/2002 | Lands et al. ............ 606/50 |
| 6,458,128 B1 | 10/2002 | Schulze |
| 6,458,130 B1 | 10/2002 | Frazier et al. |
| 6,511,480 B1 | 1/2003 | Tetzlaff et al. |
| 6,585,735 B1 | 7/2003 | Frazier et al. |
| 6,620,161 B2 | 9/2003 | Schulze et al. |
| 6,682,528 B2 | 1/2004 | Frazier et al. |
| 2003/0018331 A1 | 1/2003 | Dycus et al. |

FOREIGN PATENT DOCUMENTS

| | | |
|---|---|---|
| EP | 0 518 230 A1 | 12/1992 |
| EP | 0541930 B1 | 5/1993 |
| EP | 0572131 A1 | 12/1993 |
| EP | 0 584 787 A1 | 3/1994 |
| EP | 0623316 A1 | 11/1994 |
| EP | 0650701 A1 | 5/1995 |
| EP | 0694290 A3 | 3/1996 |
| EP | 0754437 A3 | 3/1997 |
| EP | 0717966 A1 | 6/1998 |
| EP | 0 853 922 A1 | 7/1998 |
| EP | 0887046 A3 | 1/1999 |
| EP | 0923907 A1 | 6/1999 |
| EP | 1034747 A1 | 9/2000 |
| EP | 1034748 A1 | 9/2000 |
| EP | 1025807 A3 | 10/2000 |
| EP | 1034746 A3 | 10/2000 |
| EP | 1050278 A1 | 11/2000 |
| EP | 1053719 A1 | 11/2000 |
| EP | 1053720 A1 | 11/2000 |
| EP | 1055399 A1 | 11/2000 |
| EP | 1055400 A1 | 11/2000 |
| EP | 1080694 A1 | 3/2001 |
| EP | 1082944 A1 | 3/2001 |
| GB | 2214430 A | 6/1989 |
| JP | 5-40112 | 2/1993 |
| JP | 06343644 A2 | 12/1994 |
| JP | 07265328 A2 | 10/1995 |
| JP | 08056955 A2 | 3/1996 |
| JP | 08252263 A2 | 10/1996 |
| JP | 09010223 A2 | 1/1997 |
| JP | 11249298 A2 | 9/1999 |
| JP | 2000342599 A2 | 12/2000 |
| JP | 2000350732 A2 | 12/2000 |
| JP | 2001008944 A2 | 1/2001 |
| JP | 2001029356 A2 | 2/2001 |
| JP | 2001128990 A2 | 5/2001 |
| SU | 401367 | 10/1973 |
| WO | WO 92/06642 | 4/1992 |
| WO | WO 95/02369 | 1/1995 |
| WO | WO 97/00646 | 1/1997 |
| WO | WO97/00647 | 1/1997 |
| WO | WO 97/24073 | 7/1997 |
| WO | WO 97/24993 | 7/1997 |
| WO | WO 98/27880 | 7/1998 |
| WO | WO 99/03407 | 1/1999 |
| WO | WO 99/03408 | 1/1999 |
| WO | WO 99/03409 | 1/1999 |
| WO | WO 99/40857 | 8/1999 |
| WO | WO 99/51158 | 10/1999 |
| WO | WO 00/24330 | 5/2000 |
| WO | WO 00/41638 | 7/2000 |
| WO | WO 00/53112 | 9/2000 |
| WO | WO 01/54604 A1 | 8/2001 |
| WO | WO 02/080796 A1 | 10/2002 |

OTHER PUBLICATIONS

Bergdahl et al., Studies on Coagulation and the Development of an Automatic Computerized Bipolar Conagulator, J. Neurosurg. vol. 75, Jul. 1991 pp 148–151.

Sigel et al., The Mechanism of Blood Vessel Closure By High Frequency Electrocoagulation, Surgery & Gynecology and Obstetrics, Oct. 1965 pp. 832–831.

Kennedy et al. "High–burst–strength, feedback–controlled bipolar vessel sealing",Surgical Endoscopy (1998) 12:876–878.

Peterson et al. "Comparison of Healing Proccess Following Ligation with Sutures and Bipolar Vessel Sealing", Surgical Technology International (2001).

Linehan et al. "A Phase I Study of the LigaSure Vessel Sealing System in Hepatic Surgery", Section of HPB Surgery, Washington University School of medicine, St. Louis MO, Presented ar AHPBA, Feb. 2001.

Johnson et al. "Evaluation of the LigaSure Vessel Sealing System in Hemorrhoidectormy", American College of Surgeons (ACS) Clinicla Congress Poster (2000).

Sayfan et al. "Sutureless Closed Hemorrholdectomy: A New Technique", Annals of Surgery vol. 234 No. 1 Jul. 2001 pp. 21–24.

Henlford et al. "Initial Results with an Electrothermal Bipolar Vessel Sealer", Surgical Endoscopy (2000) 15:799–801.

Henlford et al. "Initial Research and Clinical results with and Electrothermal Bipolar Vessel Sealer", Oct. 1999.

McLellan et al. "Vessel Sealing for Hemostasis During pelvic Surgery", Int'l Federation of Gynecology and Obstetrics FIGO World Congress 2000, Washington, D.C.

Levy et al. "Use of a New Energy–based Vessel Ligation Device During Vaginal Hysterectomy", Int'l Federation of Gynecology and Obstetrics (FIGO) World Congress.

Crawford et al. "Use of the LigaSure Vessel Sealling System in Urologic Cancer Surger", Grand Rounds in Urology 1999 vol. 1 Issue 4 pp. 10–17.

Rothenberg et al. "Use of the LigaSure Vessel Sealing System in Minimally Invasive Surgery in Children", Int'l Pediatric Endosurgery Group (IPEG) 2000.

Palazzo et al. "Randomized clinical trial of Ligasure versus open haemorrhoidectomy", British Journal of Surgery 2002, 89, 154–157.

"Innovative in Electrosurgery" Sales/Product Literature.

LigaSure Vessel Sealing System, the Seal of Confidence in General, Gynecologic, Urologic, and Laparoscopic Surgery Sales/Product Literature.

Carbonell et al., "Comparison of theGyrus PlasmaKinetic Sealer and the Valleytab LigaSure Device in the Hemostasis of Small, Medium, and Large–Sized Arteries" Carolinas Laparoscopic and Advanced Surgery Program, Carolinas Medical Center, Charlotte, NC.

"Reducing Needlestick Injuries in the Operating Room" Sales/Product Literature.

Chung et al., "Clinical Experience of Sutureless Closed Hemorrhoidectomy with LigaSure" Diseases of the Colon & Rectum vol. 46, No. 1 Jan. 2003.

Strasberg et a., "Use of a Bipolar Vessel–Sealing Device for Parenchymal Transaction During Liver Surgery" Journal of Gastrointestinal Surgery, vol. 6, No. 4, Jul./Aug. 2002 pp. 569–574.

Paul G. Horgan, "A Novel Technique for Parenchymal Division During Hepatectomy" The American Journal of Surgery, vol. 181, No. 3, Apr. 2001 pp. 236–237.

W. Scott Helton, "LigaSure Vessel Sealing System: Revolutionary Hemostasis Product for General Surgery" Sales/Product Literature.

Michael Choti, "Abdominoperineal Resection with the LigaSure Vessel Sealing System and LigaSure Atlas 20 cm Open Instrument" Innovations That Work, Jun. 2003.

Craig Johnson, "Use of the LigaSure Vessel Sealing System in Bloodless Hemorrhoidectomy" Innovations that Work, Mar. 2000.

Mueller et al., "Extended Left Hemicolectomy Using the LigaSure Vessel Sealing System" Innovations that Work, Sep. 1999.

Herman et al., "Laparoscopic Intestinal Resection With the LigaSure Vessel Sealing System: A Case Report" Innovations that Work, Feb. 2002.

Carus et al., "Initial Experience With The LigaSure Vessel Sealing System in Abdominal Surgery" Innovations That Work, Jun. 2002.

Levy et al. "Randomized Trial of Suture Versus Electrosurgical Bipolar Vessel Sealing in Vaginal Hysterectomy" Obstetrics & Gynecology, vol. 102, No. 1, Jul. 2003.

Levy et al., "Update on Hysterectomy—New Technologies and Techniques" OBG Management, Feb. 2003.

Barbara Levy, "Use of a New Vessel Ligation Device During Vaginal Hysterectomy" FIGO 2000, Washington, D.C.

McLellan et al. "Vessel Sealing For Hemostasis During Gynecologic Surgery" Sales/Product Literature.

Sengupta et al., "Use of a Computer–Controlled Bipolar Diathermy System in Radical Prostatectomies and Other Open Urological Surgery" ANZ Journal of Surgery (2001) 71.9 pp. 538–540.

Olsson et al. "Radical Cystectomy in Females" Current Surgical Techniques in Urology, vol. 14, Issue 3.

E. David Crawford "Use of a Novel Vessel Sealing Technology in Management of the Dorsal Veinous Complex" sales Product Literature.

Jarrett et al., "Use of the LigaSure Vessel Sealing System for Perl–Hilar Vessels in Laparoscopic Nephrectomy" Sales Product Literature.

E. David Crawford "Evaluation of a New Vessel Sealing Device in urologica Cancer Surgery" Sales Product Literature.

Joseph Ortenberg "LigaSure System used in Laparoscopic 1st and 2nd Stage Orchiopaxy" Innovations That Work, Nov. 2002.

Koyle et al., "Laparoscopic Palomo Varicocele Ligation in Children an Adolescents" Pediatric Endosurgery & innovative Techniques, vol. 6, No. 1, 2002.

Dulemba et al. "Use of a Bipolar Electrothermal Vessel Sealer in Laparoscopically Assited Vagial Hysterectomy" Sales Product Literature.

Johnson et al. "Evaluation of a Bipolar electrothermal Vessel Sealing Device in Hemorrhoidectomy" Sales Product Literature.

* cited by examiner

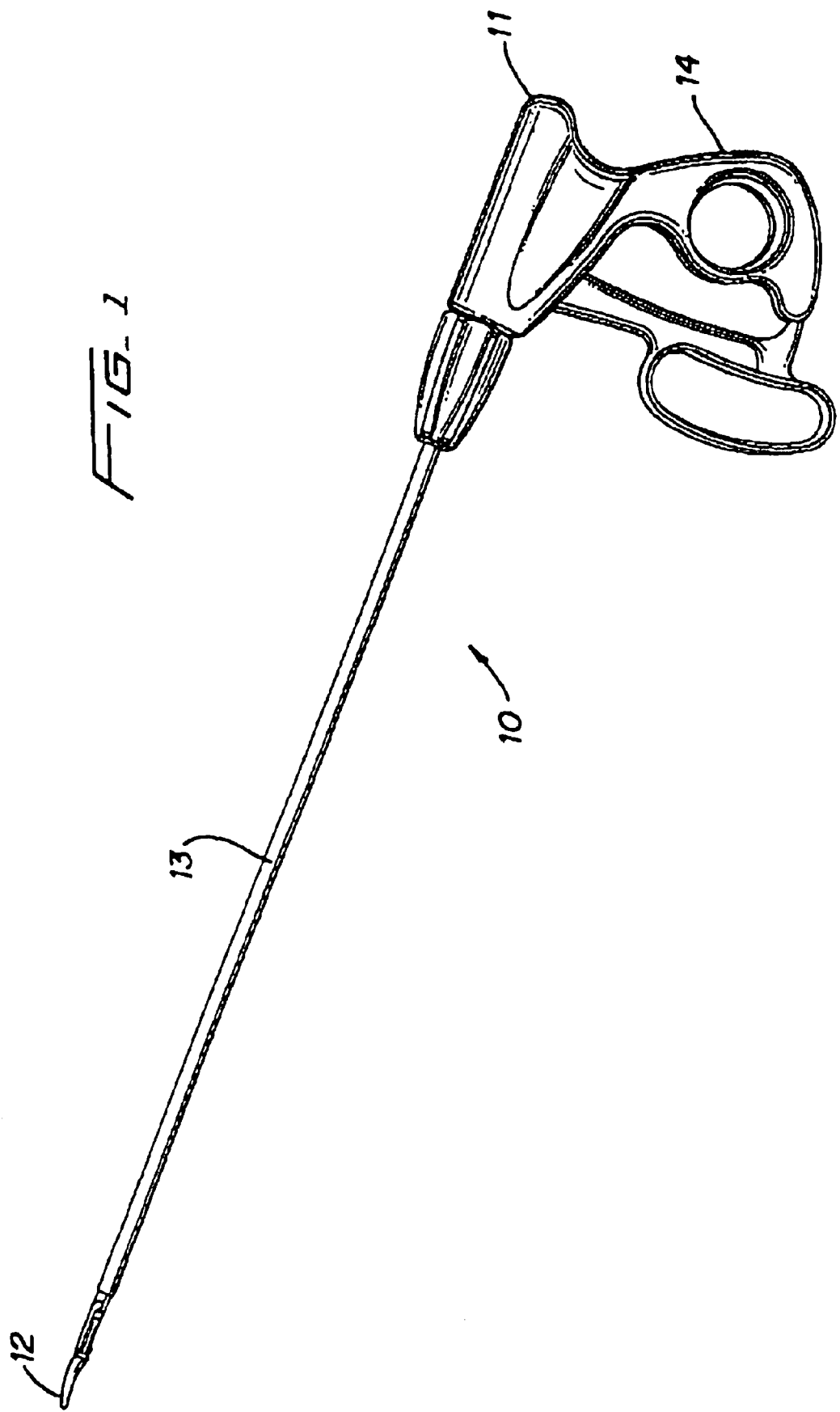

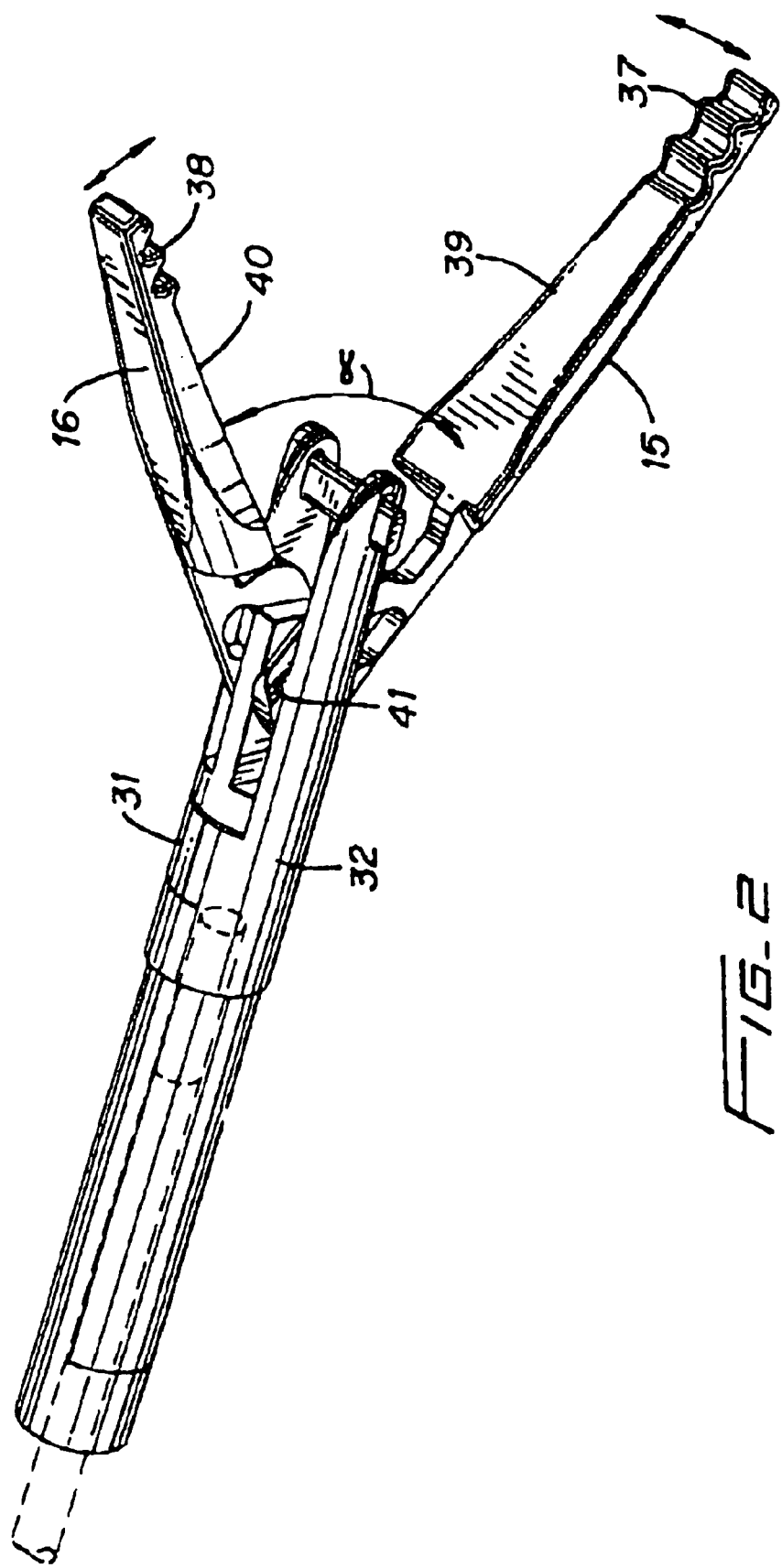

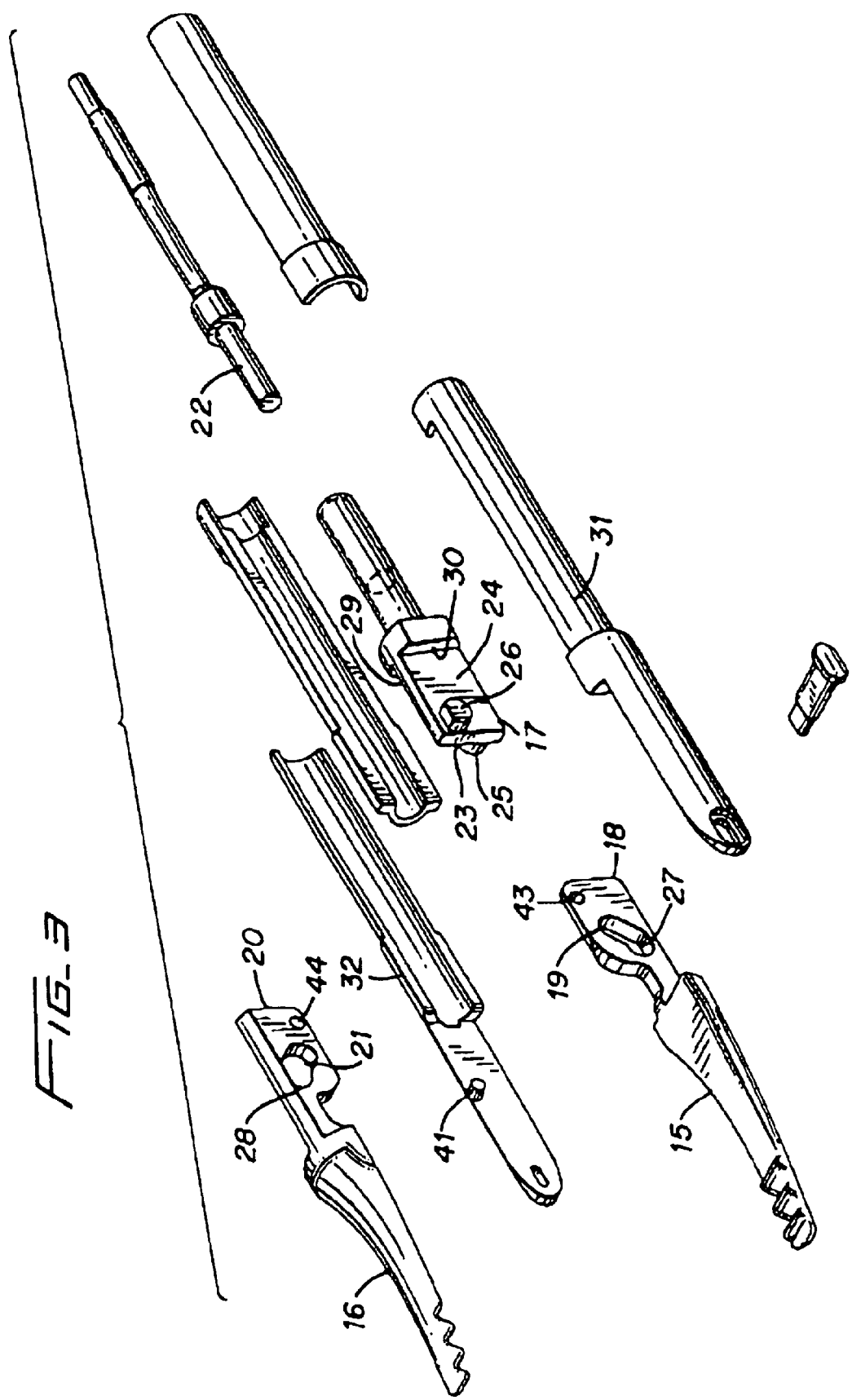

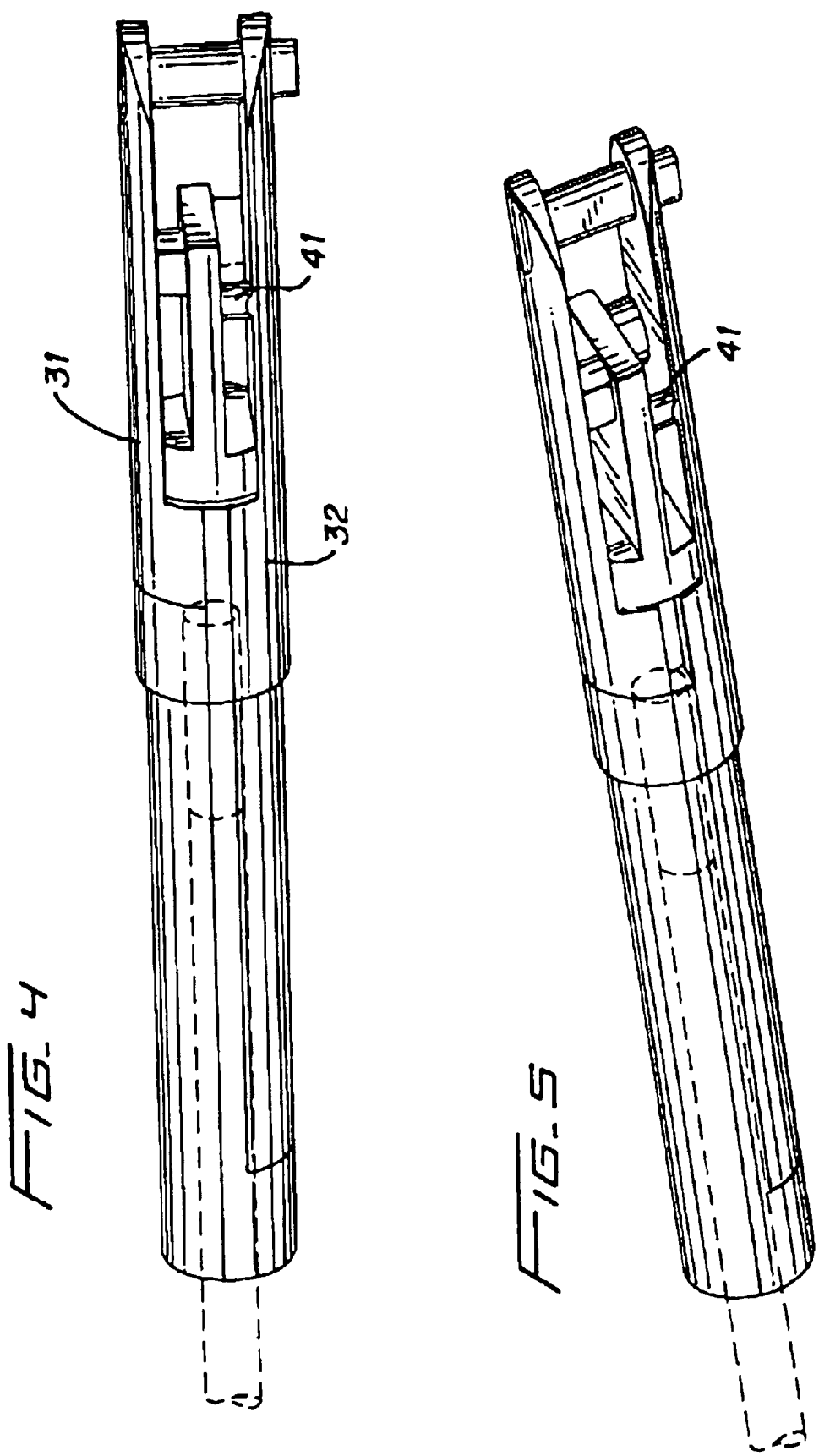

LAPAROSCOPIC BIPOLAR ELECTROSURGICAL INSTRUMENT

This application is a continuation of U.S. application Ser. No. 09/591,330 filed on Jun. 9, 2000, now U.S. Pat. No. 6,451,018, which is a continuation of U.S. application Ser. No. 08/970,472 filed on Nov. 14,1997, now U.S. Pat. No. 6,228,083.

FIELD OF THE INVENTION

This relates to an electrosurgical instrument for performing laparoscopic surgical procedures, and more particularly to a laparoscopic electrosurgical instrument that is capable of grasping vessels and vascular tissue with sufficient force between two bipolar jaws to seal the vessel or vascular tissue.

BACKGROUND OF THE DISCLOSURE

Laparoscopic surgical instruments are used to perform surgical operation without making large incisions in the patient. The laparoscopic instruments are inserted into the patient through a cannula, or port, that has been made with a trocar. Typical sizes for cannulas range from three millimeters to twelve millimeters. Smaller cannulas are usually preferred, and this presents a design challenge to instrument manufacturers who must find ways to make surgical instruments that fit through cannulas.

Certain surgical procedures require cutting blood vessels or vascular tissue. This sometimes presents a problem for surgeons because it is difficult to suture blood vessels using laparoscopic tools. Very small blood vessels, in the range below two millimeters in diameter, can often be closed using standard electrosurgical Techniques. If a larger vessel is severed, it may be necessary for the surgeon to convert the laparoscopic procedure into an open-surgical procedure and thereby abandon the benefits of laparoscopy.

Several journal articles have disclosed methods for sealing small blood vessels using electrosurgery. An article entitled *Studies on Coagulation and the Development of an Automatic Computerized Bipolar Coagulator*, J. Neurosurg., Volume 75, Jul. 1991, describes a bipolar coagulator which is used to seal small blood vessels. The article states that it was not possible to safely coagulate arteries with a diameter larger than 2 to 2.5 mm. A second article entitled *Automatically Controlled Bipolar Electrocoagulation—"COA—COMP"*, Neurosurg. Rev. (1984), pp.187–190. This article describes a method for terminating electrosurgical power to the vessel so that charring of the vessel walls can be avoided.

It has been recently determined that electrosurgical methods may be able to seal larger vessels using an appropriate electrosurgical power curve, coupled with an instrument capable of applying a large closure force to the vessel walls. It is thought that the process of coagulating small vessels is fundamentally different than electrosurgical vessel sealing. Coagulation is defined as a process of desiccating tissue wherein the tissue cells are ruptured and dried. Vessel sealing is defined as the process of liquefying the collagen in the tissue so that it crosslinks and reforms into a fused mass. Thus, coagulation of small vessels is sufficient to permanently close them. Larger vessels need to be sealed to assure permanent closure.

It would be desirable to have a surgical tool capable of applying electrosurgical energy, capable of applying a large closure force to the vessel walls, and also capable of fitting through a cannula. A large closure force between the jaws typically requires a large moment about the pivot for each jaw. This presents a challenge because the first and second pins have a small moment arm with respect to the pivot of each jaw. A large force, coupled with a small moment arm, is undesirable because the large forces may shear the first and second pins. It is also undesirable to increase the moment arm of the first and second pins because the physical size of the yoke might not fit through a cannula.

Several bipolar laparoscopic instruments are known. For example, U.S. Pat. No. 3,938,527 discloses a bipolar laparoscopic instrument for tubal cauterization. U.S. Pat. No. 5,250,047 discloses a bipolar laparoscopic instrument with a replaceable electrode tip assembly. U.S. Pat. No. 5,445,638 discloses a bipolar coagulation and cutting forceps with first and second conductors extending from the distal end. U.S. Pat. No. 5,391,166 discloses a bipolar endoscopic instrument having a detachable working end. U.S. Pat. No. 5,342,359 discloses a bipolar coagulation device.

The present invention solves the problem of providing a large closure force between the jaws of a laparoscopic bipolar electrosurgical instrument, using a compact design that fits through a cannula, without risking structural failure of the instrument yoke.

SUMMARY OF THE INVENTION

The present invention is an instrument for applying bipolar electrosurgical current to tissue in a laparoscopic operation with the added benefit of providing a large closure force between the instrument jaws. The large closure force may be particularly useful for vessel sealing operations. An advantage of the present invention is that tissue can be grasped and clamped with a relatively large closure force without damage to the yoke. The yoke is capable of transmitting the large closure force to the instrument jaws while being small enough to fit through a cannula.

The laparoscopic bipolar electrosurgical instrument comprises first and second jaws having, respectively, first and second flanges with first and second slots. The instrument is electrically connected to an electrosurgical generator, and conducts bipolar electrosurgical current to the first and second jaws. A yoke is attached to a pushrod and positioned to electrically insulate the first flange from the second flange. First and second pins on the yoke are designed to engage the first and second slots, respectively, in a cam-follower arrangement that opens and closes the jaws with linear motion of the yoke. The yoke is preferably a "push yoke" which means that linear motion of the yoke in the direction of the distal end of the instrument will cause the jaws to close together.

The yoke has first and second shoulders that are spaced apart from the first and second flanges until the jaws are in close arcuate proximity to each other. At that point, the first and second shoulders engage the first and second flanges, whereby further distal motion of the yoke applies a force to the first and second flanges that creates a moment about the pivot of each jaw. In general, the cam-follower arrangement of pins and slots may be designed to provide coarse motion of the jaws with relatively small forces. Large closure forces, once the jaws are relatively close together, may be obtained by pressing the shoulders against the flanges. The first and second pins move into cul-de-sacs in the first and second slots to protect them from large shear stresses when the shoulders are applying relatively large forces to the flanges. Thus, the first and second pins may be made from an electrically insulative material that is not designed to handle large shear stresses, large closure forces may be obtained, and the entire assembly may be compact and fit through a cannula.

A method of making the laparoscopic bipolar electrosurgical instrument is described, comprising the following steps: forming a first jaw having a first flange with a first slot, and a second jaw having a second flange with a second slot; attaching the yoke to a pushrod; electrically insulating the first flange from the second flange with the yoke; engaging first and second pins with the first and second slots; positioning first and second cul-de-sacs respectively in the first and second slots to relieve shear stresses on the first and second pins at a subtended angle and approximately wherein first and second shoulders engage the first and second flanges.

BRIEF DESCRIPTION OF THE DRAWINGS

FIG. 1 is a perspective view of a laparoscopic bipolar electrosurgical instruments.

FIG. 2 is a perspective view of the distal end and jaws of the instrument in FIG. 1.

FIG. 3 is an exploded view of the distal end shown in FIG. 2.

FIG. 4 is perspective view of the distal end of the instrument with the jaws removed.

FIG. 5 is another perspective of FIG. 4.

DETAILED DESCRIPTION OF THE INVENTION

Figure 6:
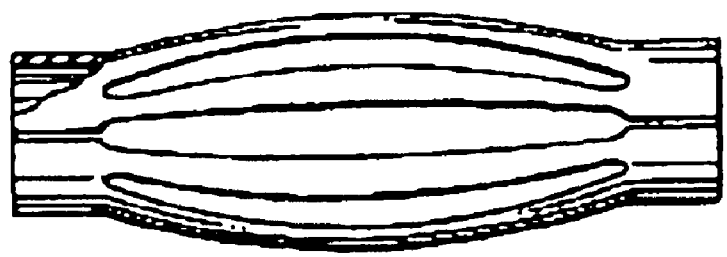
FIG. 6 is a side view of an electrical spring contact.

A laparoscopic bipolar electrosurgical instrument 10 is shown in FIG. 1. The instrument 10 has a proximal end 11 with a handle 14 for holding and manipulating the instrument 10. A distal end 12 on the instrument 10 is used for surgical manipulation of tissue. The instrument 10 comprises an elongate tube 13 that is sized to fit through a cannula for laparoscopic operations, and in different embodiments may be sized to fit through either a five or seven millimeter cannula.

A portion f the distal end 12 of the instrument 10 is shown in FIG. 2. A first jaw 15 and a second jaw 16 are shown in an open position. An angle α is subtended by the jaws 15 and 16. Closing of the jaws 15 and 16 is defined as reduction of the angle α subtended by the jaws 15 and 16. Similarly, opening of the jaws 15 and 16 is defined as an enlargement of the angle α. The angle α is zero when the jaws 15 and 16 are closed together. The center of rotation for the first jaws 15 is at the first pivot 41, and the center of rotation for the second jaw 16 is at the second pivot 42. The first pivot 41 is located on an outer nose piece 32, and fits in a first pivot hole 43 located on the first flange 18. The second pivot 42 is located on an inner nose piece 31, and fits in a second pivot hole 44 located on the second flange 20.

Pieces that comprise the distal end 12 of the instrument 10 are shown in an exploded view in FIG. 3. The first jaw 15 and the second jaw 16 are shown separated from a yoke 17. The first jaw 15 has a first flange 18 and a first slot 19 therewithin. The second jaw 16 has a second flange 20 and a second slot 21 therewithin. Each jaw 15 and 16 is preferably formed from a single piece of stainless steel or other electrically conductive material.

Referring again to FIG. 3, the yoke 17 is attached to a pushrod 22. The yoke 17 is preferably formed from an electrically insulative material such as plastic. A first side 23 of the yoke 17 faces the first flange 18. A second side 24 of the yoke 17 faces the second flange 20. When the yoke 17 is positioned between the flanges 18 and 20, the yoke 17 also acts to electrically insulate the first jaw 15 from the second jaw 16. In this manner, bipolar electrosurgical current can be conducted through tissue grasped by the jaws 15 and 16 without short circuiting between the flanges 18 and 20.

A first pin 25 is located on the first side 23 to movably engage with the first slot 19. Similarly, a second pin 26 is located on the second side 24 to movably engage with the second slot 21. Each pin and slot combination works as a cam-follower mechanical linkage. Motion of the pushrod 22 moves the yoke 17 causing pins 25 and 26 to slide within their respective slots 19 and 21. The slots 19 and 21 are angled with respect to the distal ends of the jaws 15 and 16 such that the jaws 15 and 16 move in an arcuate fashion toward and away from each other. The pins 25 and 26 are different from the pivots 41 and 42. The pins 25 and 26 provide a force against the walls of the slots 19 and 21, creating a moment about the pivots 41 and 42.

The slots 19 and 21 are arranged such that distal motion of the pushrod 22 causes the jaws 15 and 16 to move together. Distal motion of the pushrod 22 is defined as motion in the direction of the distal end 12 of the instrument 10. Once the jaws 15 and 16 are closed together, the present invention holds the jaws 15 and 16 together with a compressive force on the pushrod 22.

One of the advantages of this invention is that shear forces on the pins 25 and 26 can be offloaded to prevent mechanical failure when large forces are being transmitted to the jaws 15 and 16. Each slot 19 and 20 has a cul-de-sac 27 and 28, respectively, as shown in FIG. 3. The first cul-de-sac 28 is an enlargement of the second slot 21 near its distal end. The cam-follower motion of the pins 25 and 26 in the slots 19 and 21 will bring the pins 25 and 26 into their respective cul-de-sac 27 and 28. This position of the pins 25 and 26 leaves a very small moment arm between the pins 25 and 26 and the pivots 41 and 42. The yoke 17 has shoulders 29 and 30 that can provide a relatively large moment about the pivots 41 and 42 to effect a high closure force between the jaws 15 and 16 without a high shear forces on the pins 25 and 26, as described below.

Once the pins 25 and 26 are in the cul-de-sacs 27 and 28, the force from the yoke is transmitted to the flanges 18 and 20 by a first shoulder 29 and a second shoulder 30. The shoulders 29 and 30 abut the proximal end of the flanges 18 and 20 to cause the jaws 15 and 16 to close together. The pivots 41 and 42 are preferably made of metal and can withstand relatively high shear forces. In contrast, pins 25 and 26 are preferably made of plastic and will break under relatively high shear forces. Thus, the shoulders 29 and 30 provide a moment about the pivots 41 and 42, thereby avoiding the necessity of applying high shear forces to the pins 25 and 26 when the moment arm from the pins 25 and 26 would be small. There is an angle α at which the pins 25 and 26 enter their respective cul-de-sacs 27 and 28 and the shoulders 29 and 30 abut the flanges 18 and 20. Then angle α at which the forgoing occurs is preferably around three degrees.

The bipolar electrosurgical instrument 10 has first and second poles of alternating potential that are conducted along the instrument 10 and through tissue that is grasped between the jaws 15 and 16. The first pole is conducted from the proximal end 11 toward the distal end 12 along the pushrod 22. The second pole is conducted from the proximal end 11 toward the distal end 12 along the tube 13. The outer surface of the tube 13 is preferably coated with an electrically insulative material. There is also preferably an electrically insulative barrier between the pushrod 22 and the tube 13 to prevent short circuits in the instrument 10.

In the preferred embodiment, the distal end of the instrument 10 comprises an inner nose piece 31 and an outer nose piece 32, as shown in FIG. 2. The inner nose piece 31 is electrically connected with the pushrod 22, while the outer nose piece is electrically connected with tube 13. The inner nose piece 31 and the outer nose piece 32 capture the yoke 17, along with the first and second flanges 18 and 20, as shown in FIG. 2. The yoke 17 moves axially, along an axis defined by the tube, in a space between the inner and outer nose pieces 31 and 32. A spacer 33 maintains the separation of the nose pieces 31 and 32 at their distal ends. The nose pieces 31 and 32 provide lateral support for the flanges 18 and 20 to help ensure that the pins 25 and 26 remain within the slots 19 and 21.

Figure 7:
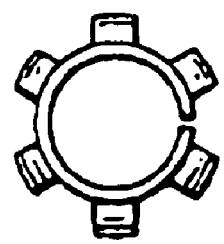
FIG. 7 is a front view of the spring contact shown in FIG. 6.

The preferred embodiment also comprises an inner insulator 34 and an outer insulator 35 for maintaining electrical insulation between the poles. The outer insulator 35 is seated between the tube 13 and the inner nose 31, as shown in FIGS. 2 and 4. The inner insulator 34 is seated between the tube 13 and the pushrod 22. In this manner, the outer nose piece 32 can provide electrical continuity between the tube 13 and the second jaw 16, while the inner nose piece 34 can provide electrical continuity between the pushrod 22 and the first jaw 15. Since the pushrod 22 Is slidably mounted within the tube 13, the preferred embodiment has a spring contact 36, as shown in FIGS. 6 and 7, mounted on the pushrod 22 to maintain an electrical connection with the inner nose piece 34 during axial motion.

The first and second jaws 15 and 16 each have ridges 37 and 38 at their distal ends that preferably nest together. The jaws 15 and 16 also have seal surfaces 39 and 40, as shown in FIG. 2. The width of the seal surfaces 39 and 40 is a parameter that affects the quality of the surgical outcome. The closure force between the jaws 15 and 16 varies along the length of the seal surfaces 39 and 40, with the largest force at the distal tip and the smallest force at the proximal end of the seal surfaces 39 and 40. It has been found through experimentation that good vessel sealing results are obtained when the closure force in grams divided by the width in millimeters is in the range of 400 to 650. Since the closure force varies with the length of the seal surfaces 39 and 40, it has been found to be advantageous to taper the width of the seal surfaces 39 and 40 along their length, with the widest width at the proximal end and the narrowest width at the distal end. This design allows the jaws 15 and 16 to apply a relatively constant closure force per unit width, preferably 525 grams per millimeter width.

A method of making a laparoscopic bipolar electrosurgical instrument 10 is also herein described. The method comprises the step of forming a first jaw 15 having a first flange 18 with a first slot 19, and a second jaw 16 having a second flange 20 with a second slot 21. The jaws 15 and 16 are preferably formed in a casting process, although it is also possible to machine the jaws 15 and 16 from stock. The casting process may include injecting powdered metal under pressure into a mold, and then applying heat.

Other steps in the method include attaching a yoke 17 to a push rod 22, and electrically insulating the first flange 18 from the second flange 20 with the yoke 17. The yoke 17 is preferably an injection molded plastic part with features including a first shoulder 29 and a second shoulder 30.

During assembly of the distal portion of the instrument 10, steps in the method include engaging a first pin 25 with the first slot 19, and engaging a second pin 26 with the second slot 21. The slots 19 and 21 are shaped such that a subtended angle α between the first and second jaws 15 and 16 decreases with distal motion of the pushrod 17, and the slots 19 and 20 are formed with cul-de-sacs 27 and 28 positioned to relive shear stresses on the first and second pins 25 and 26 at the subtended angle α approximately wherein the first and second shoulder 29 and 30 engage the first and second flanges 18 and 20.

Further steps in the method comprise: surrounding at least a portion of the pushrod 22 with an electrically conductive tube 13; electrically insulating the tube 13 from the pushrod 22; electrically connecting an inner nose piece 31 to the pushrod 22, and electrically connecting an outer nose piece 32 to the tube 13, wherein the inner nose piece 31 and the outer nose piece 32 capture the yoke 17 along with the first and second flanges 18 and 20 to conduct bipolar electrosurgical current to the first and second jaws 15 and 16. In the preferred embodiment, there is a step of electrically connecting the pushrod 22 and the inner nose piece 31 with a spring contact 36.

The method of making the instrument 10, in some embodiments, includes the step of tapering the width of the seal surfaces 29 and 40 along the length of each of the first and second jaws 15 and 16.

While a particular preferred embodiment has been illustrated and described, the scope of the protection sought is in the claims that follow.

What is claimed is:

1. A bipolar endoscopic instrument, comprising:
    a first law member adapted to be connected to a first electrical potential and a second jaw member adapted to be connected to a second electrical potential, the first and second jaw members being movable from a first position in spaced relation relative to one another to a second position wherein the first and second jaw members cooperate to conduct bipolar energy through tissue held therebetween;
    a yoke which electrically insulates the first and second jaw members during activation, the yoke including:
        a pair of pins which initially rotate the first and second jaw members from the first to second positions upon linear reciprocation of the yoke; and
        a pair of shoulder portions which are configured to abut the first and second jaw members in the second position and offload pressure on the pins during clamping and sealing of tissue.

2. The bipolar electrosurgical instrument of claim 1 further comprising:
    inner and outer nose pieces which are configured to capture the yoke and conduct bipolar electrosurgical energy to the first and second jaw members.

3. The bipolar electrosurgical instrument of claim 1 wherein the first and second jaw members include ridges which nest when the jaw members are disposed in the second position.

4. The bipolar electrosurgical instrument of claim 1 wherein each of the first and second jaw members includes a seal surface which is tapered along its respective length.

5. The bipolar electrosurgical instrument of claim 4 wherein the closure force is approximately constant along a length between the jaw members.

* * * * *